(12) United States Patent
Tonoike

(10) Patent No.: US 6,576,447 B2
(45) Date of Patent: Jun. 10, 2003

(54) METHOD FOR SYNTHESIS OF NUCLEIC ACIDS

(75) Inventor: Hiroshi Tonoike, Tsukuba (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 09/809,219

(22) Filed: Mar. 16, 2001

(65) Prior Publication Data

US 2002/0012928 A1 Jan. 31, 2002

(30) Foreign Application Priority Data

Mar. 21, 2000 (JP) .......................... 2000-77746

(51) Int. Cl.$^7$ .......................... C12P 19/34; C12Q 1/68; C07G 17/00; C12N 1/08; C07H 21/02
(52) U.S. Cl. .............. 435/91.1; 435/4; 435/5; 435/6; 435/91.2; 435/267; 435/269; 435/270; 536/23.1; 536/24.33
(58) Field of Search .................. 435/4, 5, 6, 91.1, 435/91.2, 267, 269, 270; 536/23.1, 24.33

(56) References Cited

U.S. PATENT DOCUMENTS 5,501,963 A * 3/1996 Burckhardt ............... 435/91.2

* cited by examiner

*Primary Examiner*—Jezia Riley
(74) *Attorney, Agent, or Firm*—Rader Fishman & Grauer, PLLC

(57) ABSTRACT

An object of the present invention is to provide a novel method for suppressing the action of nucleic acid synthesis inhibitory substances and thereby amplifying a nucleic acid in a sample efficiently.

According to the present invention, in a method for synthesis of nucleic acids to amplify an intended nucleic acid in a sample, the sample is brought in advance into contact with an insoluble polymer of a polyanion, a sulfated polymer or a sulfated polysaccharide, to remove nucleic acid synthesis inhibitory substances.

8 Claims, 1 Drawing Sheet

SEQUENCE LISTING

<160> NUMBER OF SEQ ID NOS: 2

<210> SEQ ID NO 1
<211> LENGTH: 26
<212> TYPE: DNA
<213> ORGANISM: Artificial Sequence
<220> FEATURE:
<221> NAME/KEY: misc_feature
<222> LOCATION: (1)..(26)
<223> OTHER INFORMATION: Artificial primer DM151 (PE Biosystems,
      Foster, USA)

<400> SEQUENCE: 1
gtctctgaat cagaaatcct tctatc                                          26

<210> SEQ ID NO 2
<211> LENGTH: 25
<212> TYPE: DNA
<213> ORGANISM: Artificial Sequence
<220> FEATURE:
<221> NAME/KEY: misc_feature
<222> LOCATION: (1)..(25)
<223> OTHER INFORMATION: Artificial primer DM152 (PE Biosystems,
      Foster, USA)

<400> SEQUENCE: 2
catgtcaaat ttcactgctt catcc                                           25

METHOD FOR SYNTHESIS OF NUCLEIC ACIDS

BACKGROUND OF THE INVENTION

1. Field of the Invention

The present invention relates to a method for synthesis of nucleic acids, especially to a method for synthesis of nucleic acids by means of a polymerase chain reaction (hereinafter abbreviated as a PCR).

2. Description of the Related Art

A PCR method is a procedure capable of amplifying an intended DNA fragment as much as several hundred thousand-fold by repeating a process comprised of dissociation of a DNA strand into single strands, binding of primers with sandwiching a particular region of the DNA strand, and a DNA synthesis reaction by the action of a DNA polymerase. The PCR method is described in Japanese Laid-open Patent Publication No.S61-274697 which is an invention by Mullis et al.

A PCR procedure can be used as a highly sensitive method for analyzing nucleic acids in various samples, and particularly it can be used in analysis of nucleic acids in a sample derived from an animal body fluid. The PCR procedure is therefore used for such a purpose of diagnosis or monitoring of an infection, a hereditary disease, and a cancer. The PCR procedure is also suited to DNA typing tests for a transplantation, a paternity test, medical treatments based on an individual genetic information, and the like. For these purposes, a peripheral blood is often selected as a test object.

One drawback of the PCR procedure is that the reaction is inhibited by pigments, proteins, saccharides, or unknown contaminants. Namely, many DNA polymerases including TaqDNA polymerase derived from *Thermus aquaticus*, a typical thermostable DNA polymerase, are widely known to allow the PCR to be inhibited potently by even a trace amount of living body-derived contaminants existing in the PCR reaction solution. Therefore, the PCR procedure requires a process in which a cell(s), a protozoan (protozoa), a fungus (fungi), a bacterium (bacteria), a virus(es) and the like (hereinafter referred to as a gene inclusion body) are isolated from a subject and then nucleic acids are extracted from the gene inclusion body prior to a DNA amplification. Such process has conventionally been a procedure in which the gene inclusion body is decomposed using an enzyme, a surfactant, a chaotropic agent, or the like, and then nucleic acids are extracted from the decomposed product of the gene inclusion body using, for example, phenol or phenol/chloroform. Recently, an ion-exchange resin, a glass filter, or a reagent having an effect of agglutinating proteins is used in the step of the nucleic acid extraction.

It is difficult, however, to completely remove impurities by purifying nucleic acids in a sample using these procedures, and furthermore, an amount of nucleic acids in a sample recovered by these purification procedures often varies among experiments. For these reasons, a subsequent nucleic acid synthesis may sometimes be unsuccessful, especially when a content of the intended nucleic acid in the sample is low. In addition, these purification procedures involve complicated manipulations and are time-consuming, and there is a high opportunity for contamination during the procedures. Therefore, a simpler, more convenient and effective method of a sample pretreatment is desired in order to solve these problems.

SUMMARY OF THE INVENTION

Thus, an object of the present invention is to provide a novel method for removing nucleic acid synthesis inhibitory substances and thereby amplifying a nucleic acid in a sample efficiently.

The present inventor found that nucleic acid synthesis inhibitory substances in a biological sample can be removed by bringing the substances into contact with an insoluble polymer of a polyanion, and thus arrived at the present invention.

The present invention is a method for synthesis of nucleic acids to amplify an intended nucleic acid in a sample which comprises bringing the sample in advance into contact with an insoluble polymer of a polymer compound having a repeating structure containing at least one anion (polyanion) and/or a salt thereof (hereinafter collectively referred to as a polyanion).

The present invention is the method for synthesis of nucleic acids wherein the polyanion is a polymer compound having a repeating structure containing at least one sulfate group (polysulfate) and/or a salt thereof (hereinafter collectively referred to as a sulfated polymer).

The present invention is the method for synthesis of nucleic acids wherein the sulfated polymer is selected from the group consisting of sulfated polysaccharides and salts thereof (hereinafter collectively referred to as a sulfated polysaccharide).

The present invention is the method for synthesis of nucleic acids wherein the sulfated polysaccharide is selected from the group consisting of heparin and a salt thereof, and dextran sulfate and a salt thereof.

The present invention is the method for synthesis of nucleic acids wherein the sample is a living body-derived sample itself.

According to the present invention, by conducting a simple and convenient treatment in which a sample, such as serum or plasma, containing a lot of PCR inhibitory substances is brought in advance into contact with an insoluble polymer of a polyanion, it becomes possible to directly amplify an intended nucleic acid efficiently without undergoing a process of isolating and purifying nucleic acids from the sample. It becomes also possible by the present invention to perform procedures for nucleic acid synthesis more simply, conveniently and rapidly, and thereby reduce the opportunity for contamination.

DETAILED DESCRIPTION OF THE INVENTION

Figure 1:
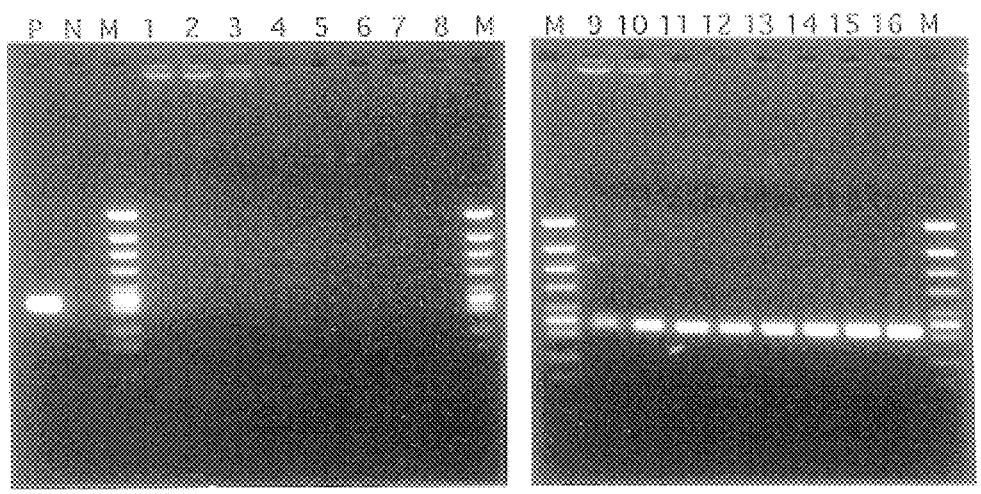
FIG. 1 shows an electrophoretogram of amplified products obtained by the PCR in which a serum is directly added to a PCR reaction solution.

The present invention is a method for synthesis of nucleic acids to amplify an intended nucleic acid in a sample which comprises bringing the sample into contact with an insoluble polymer of a polyanion prior to a nucleic acid amplification reaction.

As used herein, the term "polyanion" refers to a polymer compound and a salt thereof, having a repeating structure containing at least one anion. Examples of the anion include, but not limited to, sulfate, sulfite, phosphate, carboxyl, and thiocarboxylic groups. Particularly preferred is a polymer compound having a repeating structure containing at least one sulfate group and a salt thereof (a sulfated polymer).

As the sulfated polymer, a sulfated polysaccharide is preferred. The preferred sulfated polysaccharide includes, but not limited to, heparin and a salt thereof as well as dextran sulfate and a salt thereof. Other sulfated polysaccharides such as heparan sulfate, chondroitin sulfate, dermatan sulfate, fucoidan sulfate, funoran, sulfated agarose, carrageenan, porphyran, fucoidan, and sulfated curdlan may also be used.

The sulfated polymers other than those mentioned above may include, but not limited to, polyvinyl sulfate and a salt thereof.

Examples of the salts include, but not limited to, sodium and potassium salts.

Insoluble polymers of the polyanion may be used individually or as a combination of several kinds of such polymers. These insoluble polymers do not need to be homogeneous, and they may be composite insoluble polymers containing the polyanion, or the polyanions attached to some insoluble support.

In order to bring a sample in advance into contact with an insoluble polymer of a polyanion, various procedures may be adopted, including, but not limited to, the following methods. For example, the sample may be passed through a column packed with said insoluble polymer or through a filter made of said insoluble polymer. Alternatively, said insoluble polymer and the sample may be put into a container to mix together, and then the sample may be recovered from the container. Furthermore, the sample may also be put into a container of which inner wall is coated with said insoluble polymer or into a container which itself is made of said insoluble polymer, and then recovered from the container. As used herein, the phrase "in advance" means the step is done before an amplification reaction, and the sample is brought into contact with the insoluble polymer of the polyanion before the sample is added to a reaction solution for gene amplification.

In the present invention, the term "sample" refers to a living body-derived sample itself or a living body-derived sample which is subjected to some treatment, and the term "living body-derived sample" refers to an animal or a plant tissue, a body fluid, an excretion, and the like. The body fluids include blood, cerebrospinal fluid, saliva, and milk, and the excretions include feces, urine, and sweat, although they are not so limited. The living body-derived sample may, but not necessarily, be directly added to a reaction solution for gene amplification without particular treatments other than bringing it into contact with the insoluble polymer of the polyanion, other treatments such as a nucleic acid extraction may also be additionally adopted in combination.

The reaction solution for gene amplification conventionally contains a pH buffer as well as salts such as $MgCl_2$ and KCl, primers, deoxyribonucleotides, and a nucleic acid polymerase. The salts mentioned above may be replaced with other salts as appropriate. In addition, various substances including proteins such as gelatin and albumin and dimethyl sulfoxide are sometimes added.

The pH buffer is prepared by a combination of tris (hydroxymethyl)aminomethane and a mineral acid such as hydrochloric, nitric, or sulfuric acid, and a preferred mineral acid is hydrochloric acid. Alternatively, various other pH buffers, including pH buffers comprising a combination of Tricine, CAPSO (3-N-cyclohexylamino-2-hydroxypropanesulfonic acid), or CHES (2-(cyclohexylamino)ethanesulfonic acid) and caustic soda or caustic potash, may be used. The pH-adjusted buffer is used at a concentration between 10 mM and 100 mM in the reaction solution for gene amplification.

The term "primer" refers to an oligonucleotide that acts as an initiation site of synthesis in the presence of nucleic acids, reagents for amplification and other substances. The primer is desirably single-stranded, and a double-stranded primer may also be used. When the primer is double-stranded, it is desirable to convert it into its single-stranded form prior to the amplification reaction. The primers may be synthesized using known methods, or may be isolated from living organisms.

The term "nucleic acid polymerase" means an enzyme that synthesizes nucleic acids by adding deoxyribonucleotides or a chemical synthesis system doing so. Suitable nucleic acid polymerases include, but not limited to, DNA polymerase I derived from *E. coli*, the Klenow fragment of a DNA polymerase derived from *E. coli*, T4 DNA polymerase, TaqDNA polymerase, *T. litoralis* DNA polymerase, TthDNA polymerase, PfuDNA polymerase, and a reverse transcriptase.

Furthermore, according to the present invention, pH adjustment of the reaction solution for gene amplification produces a synergistic effect. For example, at a temperature of 25° C., the pH is 8.1 or more, and preferably from 8.5 to 9.5.

In the present invention, polyamines may also be added to the reaction solution for gene amplification.

The steps constituting a method for synthesis of nucleic acids of the present invention are not different from those steps in the conventional methods with the exception that the sample is brought into contact with the insoluble polymer of the polyanion, the sulfated polymer, or the sulfated polysaccharide, in advance of amplification of nucleic acids in the sample. Thus, a living body-derived sample is used as a template for nucleic acid synthesis directly after being treated in the manner described above, or after being subjected to the above treatment combined with other treatments such as the nucleic acid extraction. For example, when the PCR is used as a method for synthesis of nucleic acids, an intended double-stranded DNA fragment to be amplified is firstly heat-denatured into single-stranded DNAs (a denaturation step). Next, primers by which the region to be amplified is bounded are allowed to hybridize (an annealing step). Then, DNA polymerase is allowed to act in the presence of four deoxyribonucleotides (dATP, dGTP, dCTP and dTTP) to conduct a primer extension reaction (a polymerization step).

EXAMPLES

The present invention is further described in the following examples which are not intended to restrict the invention.

A human serum was passed through a spin column packed with sulfated dextran gel, Dextran beads, sulfated D5650 (SIGMA, Missouri, USA), and recovered as a sulfated dextran gel-treated serum.

To a PCR reaction solution (50 μl), 10 to 0 μl volume of an untreated serum and the sulfated dextran gel-treated serum were added to conduct the PCR. As a template for the PCR, cDNA reverse transcribed from 5,000 copies of Gene-Amplimer pAW109RNA (PE Biosystems, Foster, USA) was used. Primers for the PCR were DM151 and DM152 (PE Biosystems, Foster, USA), of which sequences are as below. The PCR using these two primers may produce a 308 bp amplification product.

DM151, SEQ ID. NO. 1
5' GTCTCTGAATCAGAAATCCTTCTATC 3'
DM152, SEQ ID. NO. 2
5° CATGTCAAATTTCACTGCTTCATCC 3

The PCR reaction solution used contained 10 mM Tris-HCl, 50 mM KCl, 1.5 mM $MgCl_2$, 200 μM each of dATP, dCTP, dGTP and dTTP, 0.4 μM each of the primers, and 1.25 units/50 μl of Taq DNA polymerase (TaKaRa Taq: Takara Shuzo, Kyoto, Japan).

The PCR involved a preheating at 94° C. for 3 minutes, 40 cycles each of which consists 30 seconds at 94° C. followed by 30 seconds at 60° C. followed by 1 minute at 72° C., and then the final polymerization at 72° C. for 7 minutes. After the completion of the PCR, 5 μl of the reaction solution was subjected to an electrophoresis on a 2.5% agarose gel in TAE (40 mM Tris-acetate, 1 mM EDTA) containing 0.5 μg/ml ethidium bromide to detect the amplification products.

FIG. 1 shows the electrophoretogram of amplified products obtained by the PCR in which serum was directly added to the PCR reaction solution. In the FIGURE, a lane M indicates size makers (250 ng of φ X174-RF DNA cleaved with HincII); a lane P indicates a positive control (without added serum); a lane N indicates a negative control; lanes 1 and 9 indicate the results obtained with 10 μl serum; lanes 2 and 10 indicate the results obtained with 5 μl serum; lanes 3 and 11 indicate the results obtained with 2.5 μl serum; lanes 4 and 12 indicate the results obtained with 1.25 μl serum; lanes 5 and 13 indicate the results obtained with 0.63 μl serum; lanes 6 and 14 indicate the results obtained with 0.31 μl serum; lanes 7 and 15 indicates the results obtained with 0.16 μl serum; and lanes 8 and 16 indicate the results obtained with 0.08 μl serum. The lanes 1 to 8 indicates the results obtained with the untreated serum and the lanes 9 to 16 indicate the results obtained with the sulfated dextran gel-treated serum.

As a result, it can be seen that the untreated serum exhibits extremely potent PCR inhibition so that no PCR amplification product is obtained with any amount of added serum, whereas the sulfated dextran gel-treated serum satisfactorily provides the PCR amplification product with any of the amounts of added serum.

having a repeating structure containing at least one sulfate group (polysulfate) and/or a salt thereof (hereinafter collectively referred to as a sulfated polymer).

4. The method for synthesis of nucleic acids according to claim 3, wherein the sulfated polymer is selected from the group consisting of sulfated polysaccharides and salts thereof (hereinafter collectively referred to as a sulfated polysaccharide).

5. The method for synthesis of nucleic acids according to claim 4, wherein the sulfated polysaccharide is selected from the group consisting of heparin and a salt thereof, and dextran sulfate and a salt thereof.

6. The method for synthesis of nucleic acids according to any one of claims 1 to 5, wherein the sample is a living body-derived sample itself.

7. The method for synthesis of nucleic acids according to claim 1, wherein contact of the sample in advance with the insoluble polymer of the polyanion is conducted by any one or combination of the following procedures (1) to (3):

(1) passing the sample through a column packed with said insoluble polymer or through a filter made of said insoluble polymer,

What is claimed is:

1. A method for synthesis of nucleic acids to amplify an intended nucleic acid in a sample which comprises bringing the sample in advance into contact with an insoluble polymer, said insoluble polymer containing, as part of a repeating polymer structure, at least one anion (polyanion) and/or a salt thereof (hereinafter collectively referred to as a polyanion).

2. The method for synthesis of nucleic acids according to claim 1, wherein the polyanion contains at least one sulfate group, at least one sulfite group, at least one phosphate group, at least one carboxyl group or at least one thiocarboxyl group as the anion.

3. The method for synthesis of nucleic acids according to claim 1, wherein the polyanion is a polymer compound (2) putting said insoluble polymer and the sample into a container to mix together, and then recovering the sample from the container, or (3) putting the sample into a container of which inner wall is coated with said insoluble polymer, or into a container which itself is made of said insoluble polymer, and then recovering the sample from the container.

8. A method for synthesis of nucleic acids to amplify an intended nucleic acid in a sample which comprises bringing the sample in advance into contact with an insoluble polymer, said insoluble polymer containing at least one anion (polyanion) and/or a salt thereoff which is attached to an insoluble support.

* * * * *